(12) United States Patent
Paul et al.

(10) Patent No.: US 9,359,287 B2
(45) Date of Patent: Jun. 7, 2016

(54) PROCESS FOR RECOVERING NOBLE PRODUCTS IN A PROCESS FOR PRODUCING DIALKYLAMINOALKYL (METH) ACRYLATES

(75) Inventors: Jean-Michel Paul, Metz (FR); Andre Levray, Porcelette (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/346,802

(22) PCT Filed: Sep. 11, 2012

(86) PCT No.: PCT/FR2012/052025
§ 371 (c)(1),
(2), (4) Date: Jun. 23, 2014

(87) PCT Pub. No.: WO2013/045786
PCT Pub. Date: Apr. 4, 2013

(65) Prior Publication Data
US 2014/0350291 A1    Nov. 27, 2014

(30) Foreign Application Priority Data

Sep. 27, 2011 (FR) ..................................... 11 58587

(51) Int. Cl.
*C07C 227/40* (2006.01)
*C07C 227/18* (2006.01)
*C07C 213/10* (2006.01)
*C07C 67/327* (2006.01)
*C07C 213/06* (2006.01)

(52) U.S. Cl.
CPC ............. *C07C 227/40* (2013.01); *C07C 67/327* (2013.01); *C07C 213/06* (2013.01); *C07C 213/10* (2013.01); *C07C 227/18* (2013.01)

(58) Field of Classification Search
CPC .. C07C 227/18; C07C 227/40; C07C 213/06; C07C 213/10; C07C 67/327
USPC .......................................... 560/172; 564/497
See application file for complete search history.

(56) References Cited

U.S. PATENT DOCUMENTS

| 7,268,251 | B2 | 9/2007 | Geisendoerfer et al. |
| 2007/0270606 | A1 | 11/2007 | Riondel et al. |
| 2009/0203938 | A1 | 8/2009 | Croizy et al. |

FOREIGN PATENT DOCUMENTS

FR      2 811 986 A1    1/2002

*Primary Examiner* — Shailendra Kumar
(74) *Attorney, Agent, or Firm* — Lynn B. Morreale

(57) ABSTRACT

The invention relates to a process for recovery of noble products from heavy (meth)acrylic fractions generated during production of (meth)acrylic esters by transesterification, the heavy fractions comprising at least noble products and Michael adducts, the process comprising the steps of: (i) adding at least one antifouling agent and optionally a viscosity-reducing compound to the heavy fractions; (ii) submitting the mixture to temperature and distillation conditions sufficient to crack the Michael adducts into their components; and (iii) recovering the noble products in the form of a stream of distillate, and of a final residue that is sufficiently fluid to be transported by pump.

13 Claims, 1 Drawing Sheet

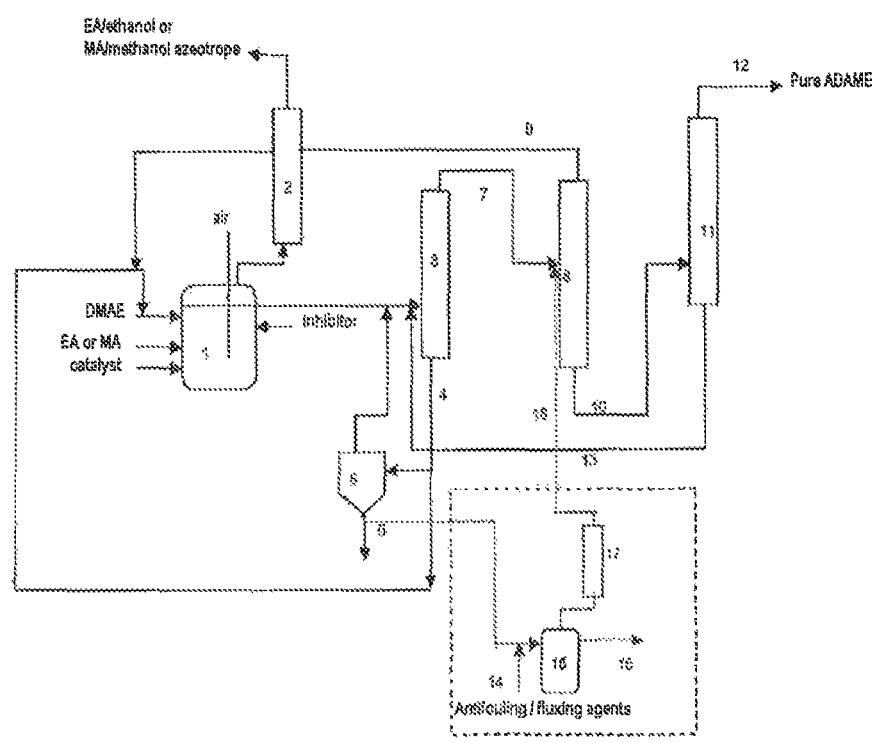

PROCESS FOR RECOVERING NOBLE PRODUCTS IN A PROCESS FOR PRODUCING DIALKYLAMINOALKYL (METH) ACRYLATES

CROSS-REFERENCE TO RELATED APPLICATIONS

This application is a national stage application under 35 U.S.C. §371 of PCT/FR2012/052025, filed Sep. 11, 2012, which claims benefit to French patent application FR 11.58587, filed on Sep. 27, 2011.

FIELD OF TECHNOLOGY

The present invention relates to the manufacture of dialkylaminoalkyl(meth)acrylate, in particular N,N-dimethylaminoethyl acrylate, by transesterification reaction of an alkyl (meth)acrylate with an amino alcohol, and relates more particularly to a process for recovering the heavy byproducts generated during said manufacture, permitting the recycling of noble products to the dialkylaminoalkyl(meth)acrylate purification unit.

BACKGROUND OF THE INVENTION

The dialkylaminoalkyl(meth)acrylates corresponding to formula (I):

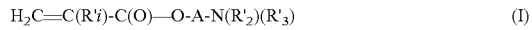
$$H_2C=C(R'i)-C(O)-O-A-N(R'_2)(R'_3) \qquad (I)$$

in which:
R'i is a hydrogen atom or a methyl radical
A is a linear or branched. $C_1$-$C_5$ alkylene radical
R'$_2$ and R'$_3$, which may be identical or different, each represent a $C_1$-$C_4$ alkyl radical,
are generally obtained by a transesterification reaction between an amino alcohol, of formula (II):

$$HO-A-N(R'_2)(R'_3) \qquad (II)$$

in which A, R'$_2$ and R'$_3$ are as defined above, and a light alkyl(meth)acrylate of formula (III):

$$CH_2=C(R'i)-COOR'_4 \qquad (III)$$

in which R'i is as defined above and R'$_4$ represents the methyl or ethyl radical.

The reaction is generally carried out in a stirred reactor in the presence of a transesterification catalyst and at least one polymerization inhibitor and the light alkyl(meth)acrylate/light alcohol R'$_4$OH azeotropic mixture generated during transesterification is withdrawn continuously during the reaction.

The problems that arise during manufacture of the dialkylaminoalkyl(meth)acrylates, notably the formation of heavy byproducts resulting from Michael addition reactions between the compounds present in the reaction mixture, will now be described, for convenience, on the basis of the example of N,N-dimethylaminoethyl acrylate (designated ADAME hereinafter) corresponding to the following formula (Ia):

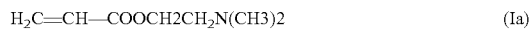
$$H_2C=CH-COOCH2CH_2N(CH3)2 \qquad (Ia)$$

obtained by transesterification reaction between a light alkyl acrylate and N,N-dimethylaminoethanol (DMAE).

The problems and the solution proposed by the invention are the same in the case when on the one hand a light alkyl methacrylate, or on the other hand amino alcohols other than DMAE, are used in the transesterification reaction.

The industrial process for manufacturing ADAME, such as that described for example in the applicant's patents EP 0960 0877 or FR 2 811 986, consists of a transesterification reaction between ethyl acrylate (EA) or methyl acrylate (MA) and N,N-dimethylaminoethanol (DMAE).

This reaction is generally catalyzed by tetraalkyl titanate such as tetraethyl titanate in solution in the DMAE in the case of the ADAME prepared starting from EA, and by a tin derivative (dibutyltin oxide (DBTO) or distannoxane) in the case of ADAME prepared starting from MA.

The reaction is generally carried out in the presence of a polymerization inhibitor and in the presence of air depleted to 8% oxygen (% by volume).

The light alcohol, methanol or ethanol, that forms during the reaction is distilled as it is formed, in the form of an MA/methanol or EA/ethanol azeotrope. This process can be carried out as a batch process or continuously, for example in a stirred reactor.

The crude reaction product generally contains the ADAME produced, unreacted light ester (EA or MA), light alcohol generated (ethanol or methanol), residual DMAE alcohol, heavy byproducts, the catalyst, and the polymerization inhibitors.

Regarding the side reactions leading to the formation of heavy byproducts during the manufacture of (meth)acrylic monomers, there is notably a reaction of Michael addition of a molecule containing a labile hydrogen atom (such as an alcohol) on the double bond of a (meth)acrylic compound.

For example, in the case of the manufacture of ADAME, the DMAE alcohol that has not yet reacted or the light alcohols formed (methanol or ethanol) add onto the double bond of the ADAME already formed or of the unreacted light acrylate (MA or EA), to form heavy byproducts of Michael addition [DMAE+ADAME] of formula:

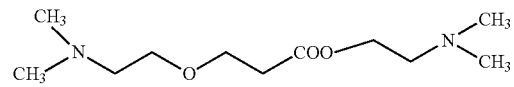

or [DMAE+MA/EA] of formula:

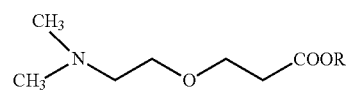

R=$CH_3$ or $C_2H_5$

A Michael addition of the DMAE alcohol on oligomers of ADAME or of EA or of MA is also possible.

A characteristic of these heavy byproducts is that their boiling point is above the boiling points of the products used in the reaction and of the desired ADAME.

In the conventional process, generally the transesterification reaction is followed by various purification steps, generally by distillation, for final recovery of the purified ADAME.

One method consists for example of submitting the crude reaction product to a distillation (tailing to remove the catalyst and the heavy products) in order to separate the ADAME with the residual light products at the top of the distillation column, and the catalyst, the heavy byproducts, the polymerization inhibitors with a minor fraction of ADAME and of DMAE and traces of light compounds at the bottom of the distillation column.

The compounds distilling at the top of the tailing column are then separated in two other distillation columns in series (topping and final rectification) to recover pure ADAME at the top of the last column.

The bottom fraction from the tailing column can be sent to a film evaporator in order to recover and recycle the traces of light compounds. The bottom fraction from the evaporator is then generally discarded.

The presence of the heavy byproducts in this fraction that is discarded poses a treatment problem, as the heavy byproducts must be incinerated for disposal. There is also a problem of large losses of raw materials (notably DMAE) and of finished product (ADAME), which are present in this fraction in free form or in the form of Michael adducts.

To recover the upgradable products present in a residue from separation of the catalyst in a process for producing (meth)acrylic esters by transesterification, it was proposed in document U.S. Pat. No. 7,268,251 to treat the residue thermally according to a method comprising the following steps:
    step 1: cracking the residue in the presence or absence of a catalyst at a temperature of 100-220° C. The light products from cracking are then recycled to one of the distillation columns of the purification train.
    step 2: the residue from step 1 comprising the polymerization inhibitors, polymers and the catalyst, is submitted to a transesterification reaction at 80-150° C. in the presence of a heavy alcohol such as glycerol of 2-ethylhexanol in order to adjust the viscosity of this fraction and make the residue pumpable. The light products generated are recycled to the reaction.

The process described in this document for recovering the upgradable materials contained in the residue of heavy byproducts is difficult to implement and has the following drawbacks:
    the residue from the first step is very viscous and therefore difficult to transport by pump; that is why it must be modified by post-transesterification;
    there is severe fouling of the cracking reactor, necessitating frequent cleaning with large decreases in heat exchange capacities;
    cleaning is very difficult because the fouling materials adhere very strongly to the wall of the cracking reactor;
    the light alcohols generated in step 2 of post-transesterification are recycled with considerable risk of contamination by the impurities present in the heavy alcohol used in this step;
    the introduction of a heavy alcohol that is completely alien to the products naturally present in the ADAME facility imposes management constraints and presents risks of contamination.

To tackle the problem of deposition of heavy compounds during the synthesis, purification or regeneration of (meth) acrylic monomers, document FR 2 876 374 proposes the use of phosphorus-containing antifouling agents; however, there is no question in this document of recovering the noble products from a heavy fraction generated during the production of (meth)acrylic esters by transesterification, leading to a fluid final residue.

In the process for synthesis of $C_i$-$C_4$ alkyl(meth)acrylates described in document FR 2 901 272, the heavy byproducts are upgraded on the basis of a treatment of distillation/thermal cracking of a bottom product. This document relates to a synthesis by direct esterification in the presence of sulfuric acid, and the operation of thermal cracking also requires the presence of sulfuric acid.

Therefore there is still a need for a simplified process for recovery of the upgradable compounds contained in a residue of heavy (meth)acrylic byproducts.

One of the aims of the present invention is therefore to upgrade the noble products (starting compounds or finished product) potentially recoverable from the heavy fraction generated in a process for synthesis of (meth)acrylic esters by transesterification. This upgrading leads to improvement of the materials balance of the process and to reduction of the final amounts of residue to be incinerated, and consequently it represents an economic advantage.

The present invention relates to a treatment process for upgrading heavy fraction containing distillable or potentially distillable products after cracking, said process only requiring a moderate number of steps without fouling the equipment used and producing a final residue of low enough viscosity to be transported by pump an incinerated.

The process of the invention is particularly advantageous compared to the process described in U.S. Pat. No. 7,268,251 since it does not employ heavy alcohol that is alien to the process, thus avoiding the risk of contamination by recycling the compounds recovered.

SUMMARY OF THE INVENTION

The present invention therefore relates to a process recovery of noble products from heavy (meth)acrylic fractions generated during the production of (meth)acrylic esters by transesterification, the heavy fractions comprising at least the noble products and Michael adducts resulting from reactions of addition on the (meth)acrylic double bonds, said process comprising the steps of:
    (i) adding at least one antifouling agent and optionally a viscosity-reducing compound to the heavy fractions;
    (ii) submitting the mixture to a sufficient temperature and to distillation conditions for cracking the Michael adducts into their constituent components;
    (iii) recovering the noble products in the form of a stream of distillate, and of a final residue that is sufficiently fluid to be transported by means of a pump.

"Noble products" are products whose recycling is useful for optimizing the economic balance of an industrial process.

The expression "heavy fraction" used in the definition of the invention is a stream, generally a residue obtained at the bottom of a distillation column, comprising heavy byproducts whose boiling point is above the boiling points of the products employed in the reaction and of the desired product. They are notably Michael adducts, formed as explained above, as well as oligomers or polymers that have formed. The heavy fraction also generally comprises the transesterification catalyst as well as the polymerization inhibitors added to the reaction, as well as a minor fraction of noble products and traces of light compounds.

In this particular case, the heavy fraction submitted to the process according to the invention comprises, as noble products, the unreacted reactants, i.e. the light alkyl(meth)acrylate (EA or MA) and the alcohol, as well as the (meth)acrylate ester produced, recycling of which makes it possible to increase the productivity of the (meth)acrylic ester manufacturing process.

The process of the invention is particularly suitable for optimizing the productivity and the economic balance of a process for manufacturing dialkylaminoalkyl(meth)acrylates by transesterification of a light alkyl(meth)acrylate with an amino alcohol, preferably of a process for manufacturing N,N-dimethylaminoethyl acrylate (ADAME) by transesterification reaction between a light alkyl acrylate and N,N-dimethylaminoethanol (DMAE).

The process according to the invention can be carried out in batch (discontinuous) mode or continuously.

The heavy fraction submitted to the process according to the invention then comprises, as noble products, at least one dialkylaminoalkyl(meth)acrylate and an amino alcohol, preferably at least N,N-dimethylaminoethyl acrylate and N,N-dimethylaminoethanol (DMAE).

A second object of the invention therefore consists of a process for manufacturing a dialkylaminoalkyl(meth)acrylate of formula (I):

in which:
R'i is a hydrogen atom or a methyl radical
A is a linear or branched $C_1$-$C_5$ alkylene radical
R'$_2$ and R'$_3$, which may be identical or different, each represent a $C_1$-$C_4$ alkyl radical, by transesterification reaction between an amino alcohol of formula (II):

in which A, R'$_2$ and R'$_3$ are as defined above, and a light alkyl(meth)acrylate of formula (III):

in which R'i is as defined above and R'$_4$ represents the methyl or ethyl radical;

said process comprising at least the following steps:
a) submitting a reaction mixture comprising a compound of formula (III), an amino alcohol of formula (II), a transesterification catalyst, and at least one polymerization inhibitor, to transesterification conditions to form a mixture of products comprising the (meth)acrylic ester (I), the unreacted compounds (II) and (III), the catalyst, the polymerization inhibitor, Michael adducts resulting from reactions of addition on the (meth)acrylic cable bonds, and other heavy compounds such as oligomers or polymers;
b) distilling the mixture of products, recovering, at the top, a stream composed essentially of the required (meth)acrylic ester (I) and light products, comprising a minor fraction of Michael adducts and of heavy products, but free or almost free from catalyst, and leaving, at the bottom, a heavy fraction comprising the catalyst, the polymerization inhibitor, the Michael adducts and the heavy compounds, with a minor fraction of the required (meth)acrylic ester (I) and of the amino alcohol and traces of light products;
c) purifying the overhead stream so as to obtain the purified dialkylaminoalkyl(meth)acrylate (I);
d) submitting at least a proportion of the heavy fraction to a process for recovery of the noble products comprising the steps of: (i) introducing at least one antifouling agent and optionally a viscosity-reducing compound; (ii) submitting the mixture to a sufficient temperature and to distillation conditions for cracking the Michael adducts into their constituent components; (iii) recovering the noble products in the form of a stream of distillate, and of a final residue that is sufficiently fluid to be transported by means of a pump;
e) recycling, to the purification step c), at least a proportion of said stream of distillate comprising at least one compound selected from the (meth)acrylic ester (I), the amino alcohol (II) or the alkyl(meth)acrylate (III);
f) disposal of the final residue for example by incineration.

According to one embodiment of the invention, the purification step c) is carried out using two distillation columns in series, and at least a proportion of the stream of distillate from step d) is recycled to the top of the first purification column.

FIG. 1 is a schematic of an embodiment of an installation according to the invention for a continuous process for producing ADAME by transesterification starting from EA and DMAE.

The invention is advantageously implemented for producing N,N-dimethylaminoethyl acrylate (ADAME) by transesterification reaction between methyl acrylate (MA) or ethyl acrylate (EA) and N,N-dimethylaminoethanol (DMAE).

A more detailed, nonlimiting description of the invention is now presented below, referring to the accompanying FIG. 1, which shows schematically a preferred embodiment of an installation according to the invention for a continuous process for producing ADAME by transesterification starting from EA and DMAE.

DETAILED DESCRIPTION OF THE INVENTION

For carrying out the invention, in a first step (i), an antifouling agent is used, whose role is to prevent agglomeration of the solid particles present in the heavy fraction and deposition of them on the walls of the equipment used.

A viscosity-reducing compound (so-called "fluxing agent") can also be added, whose role is to ensure fluidity of the final residue so that it can be transported by pump.

One or more polymerization inhibitors are generally already present in the heavy fraction, but it is possible to add them to the heavy fraction to be treated to prevent any polymerization reaction in the equipment.

As antifouling agent, a compound is selected such that its effectiveness and its effect on the viscosity of the mixture are suitable for the matrix in which it is introduced.

The compounds of formula (A) can advantageously be used as antifouling agent:

in which:
R$^1$ represents a $C_3$-$C_{30}$ alkyl radical, an aryl radical or an alkaryl radical, and these radicals can be interrupted or attached to the oxygen of the molecule by a chain —(OR$^4$)$_o$— where the R$^4$ each represent independently an ethylene, propylene or butylene chain and o is an integer from 1 to 50;
R$^2$ represents R$^1$, a hydrogen atom or a counter-ion;
R$^3$ represents a hydrogen atom or a counter-ion;

The compounds of formula (A) are notably selected from those an which R$^1$ and R$^2$ each represent independently the radical

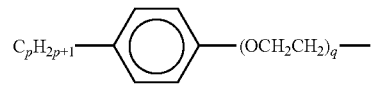

where p is an integer from 4 to 12, preferably 8 or 9, and q is an integer from 4 to 50, preferably from 6 to 20; and R$^3$ represents a hydrogen atom or a counter-ion;

and/or those in which $R^1$ represents the radical

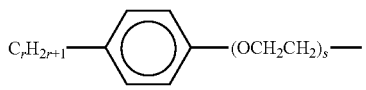

where r is an integer from 4 to 12, preferably 8 or 9, and s is an integer from 4 to 50, preferably from 6 to 20; and $R^2$ and $R^3$ each represent independently a hydrogen atom or a counter-ion.

As counter-ion included in the definition of $R^2$ and $R^3$, we may mention those resulting from neutralization of the OH function in the case when $R^2$ and/or $R^3$=H by the alkanolamines and the hydroxides of alkali metals or alkaline-earth metals. As particular examples, we may mention $N^+(CH_2CH_2OH)3$, $Na^+$ and $K^+$.

The compound or compounds (A) can be introduced as they are in the heavy fraction. They can also be introduced in solution in a solvent, or in solution in one of the (meth)acrylic monomers of the process.

The compound or compounds (A) can be introduced at a concentration in the range from 0.01 to 1 wt %, notably from 0.1 to 1 wt %, preferably from 0.1 to 0.5 wt % in the heavy fraction to be treated.

Among the antifouling agents that can be used, we may mention nonlimitatively the products marketed by the company CECA under the brand name BEYCOSTATS®, and more particularly BEYCOSTAT® FB 095.

Surprisingly, the compounds of formula (A) proved to be effective as antifouling agents, despite the nature of the heavy fractions, notably the heavy fractions of a process for synthesis of ADAME starting from dimethylaminoethanol. In fact, these fractions contain the transesterification catalyst. In this environment, there is a risk of the amino alcohol reacting with the antifouling agent, in particular of a phosphoric ester nature, which can lead to the formation of a dimethylaminoethyl phosphate, whose chemical structure no longer has dispersant properties owing to disappearance of the hydrophilic and hydrophobic groups of the starting phosphoric ester.

As viscosity-reducing compounds, it is possible to use any liquefying compound that is able to lower the viscosity to around 200 centipoise at 80° C. for the final residue.

A viscosity-reducing compound that can be used is for example the product marketed by the company NALCO under the designation NALCO® EC 3368A.

The viscosity-reducing compound is added to the heavy fraction in sufficient amount so that the final residue from step (ii) of the process according to the invention is pumpable. This amount is generally between 0.01 and 0.5 wt %.

As a variant, it is possible to add, to the heavy fractions, according to step (i) of the process of the invention, a single compound acting simultaneously as antifouling agent and as viscosity-reducing agent. In this case it is possible to use, for example, the product marketed by the company NALCO under the designation NALCO® EC 3363A.

The heavy fraction can contain various polymerization inhibitors, among which we may mention phenothiazine (PTZ), hydroquinone (HQ) and its derivatives such as hydroquinone methyl ether, 2,6-di-tert-butyl-4-methylphenol (BHT), the N-oxyl compounds of the 4-hydroxy-2,2,6,6-tetramethyl piperidinoxyl (4-OH TEMPO) type and mixtures thereof in all proportions. Advantageously, an amount of polymerization inhibitor in the range from 500 to 5000 ppm will be added in step (i).

Implementation of the invention according to step (ii) is done by heating the heavy fraction with additive to a temperature in the range from 100° C. to 250° C., preferably from 150 to 200° C. for removing, by distillation, the noble products present initially and the noble products that result from thermal cracking of the Michael abducts.

The operation of thermal cracking according to step (ii) of the process of the invention can be carried out without further addition of catalyst to the heavy fraction to be treated, in particular without adding acid catalyst, which limits the side reactions with the antifouling agent added.

In a preferred variant of the invention, before step (i) of adding the antifouling agent, the heavy fraction is sent beforehand to a film evaporator in order to recover and recycle the light compounds that are present in trace amounts.

The noble products, essentially the required (meth)acrylic ester and the unreacted alcohol, are recovered according to step (iii) by distillation under atmosphere of nitrogen or of air depleted to 8 vol % of oxygen and under reduced pressure, for example from 10 to 50 mbar. The use of nitrogen is preferred.

The treatment can be carried out in batch or continuous mode in a double-jacketed reactor or in a still surmounted by a column which in particular performs the role of splash head in order to limit the rise of the inhibitors.

The residence time is generally between 30 min and one hour.

The noble products thus recovered are utilized by recycling them to the installation, at various steps of the process, preferably in step (c) of purification of the crude reaction product.

The final residue is then cooled to 60° C.; it is in principle sufficiently fluid to be transported by pump directly. Nevertheless, from 5 to 30% of solvent, preferably methanol, can be added to this residue to facilitate transport by pump at this temperature.

The final residues are then incinerated.

A preferred embodiment of the invention will now be described in more detail, referring to the accompanying FIG. 1 for a continuous process for producing ADAME by transesterification starting from EA and DMAE, in which steps (a) to (f) are applicable more generally to the production of the (meth)acrylates of formula (I) by transesterification starting from the alkyl(meth)acrylates of formula (III) and amino alcohol (II), defined in the process according to the invention.

According to a first step (a), the transesterification reaction between EA and DMAE is carried out in reactor 1 in the presence of a catalyst, preferably tetraethyl titanate, and polymerization inhibitors. Reactor 1 is surmounted by a distillation column 2 to remove the light alcohol formed (ethanol) as it is formed and thus shift the equilibrium or the reaction toward the formation of ADAME.

According to step (b) of the process, the reaction mixture is submitted to distillation in a distillation column (tailing column 3). At the top of column 3, a stream 7 is recovered that is free from the catalyst and the polymerization inhibitors and comprises the ADAME produced and light compounds with a minor fraction of Michael adducts and heavy products.

A heavy fraction 4 comprising the catalyst, the polymerization inhibitors, the Michael adducts and the heavy compounds such as oligomers and polymers with a minor fraction of ADAME and of DMAE and traces of light compounds is recovered at the bottom of column 3.

According to step (c) of the process, stream 7 is submitted to purification, which is carried out by means of distillation column 8, whose overhead stream 9 is recycled to the reaction, the bottom stream 10 being sent to a distillation column 11 for obtaining the purified ADAME 12 at the top and, at the bottom, a stream 13 rich in inhibitors, which is recycled to the stream of crude reaction mixture feeding column 3.

According to step (d) of the process, the heavy fraction 4 from the bottom of column 3, which notably contains the catalyst, is partly recycled to the reactor 1 and partly submitted to the process according to the invention for recovery of the noble products (ADAME and DMAE) in reactor 15.

The heavy fraction can first be concentrated on a film evaporator 5, for separating the traces of light compounds, which are then recycled to the feed of column 3. The heavy fraction 6 from the evaporator is then sent to reactor 15 after adding an antifouling agent and optionally a viscosity-reducing compound.

The reactor 15 can be of the double-jacketed reactor type or a still surmounted by a distillation column 17 of low efficiency (1 to 3 theoretical plates), which rather performs the role of splash head.

In reactor 15, the heavy fraction, notably comprising the Michael adduct [DMAE–ADAME] which results from addition of DMAE on ADAME, undergoes thermal cracking to recover a stream 18 rich in DMAE and ADAME at the top of column 17, which is recycled, according to step (e) of the process, to the inlet of the ADAME purification column 8.

In the last step (f), the final residues 16 are incinerated.

Examples of compositions of streams in this process for manufacturing ADAME are:
heavy fraction 6 generally contains about 1 to 20% of DMAE, 10 to 30% of ADAME, 10 to 35% of Michael adducts [DMAE–ADAME], the remainder essentially consisting of other heavy byproducts, polymers, catalyst and polymerization inhibitors.

The process according to the invention makes it possible to recover, by simple distillation, more than 90 wt % of the noble products (ADAME and DMAE) contained in fraction 6 from the evaporator 5, and to crack respectively to ADAME/DMAE, and DMAE/EA, 30 mol % of the Michael adducts [DMAE+ADAME] and [DMAE+EA].

The following examples illustrate the present invention but without limiting its scope.

EXAMPLES

The percentages are expressed in percentages by weight.
The following abbreviations are used:
EA: ethyl acrylate
DMAE: N,N-dimethylaminoethanol
ADAME: N,N-dimethylaminoethyl acrylate
APA: Michael adduct resulting from addition of DMAE on ADAME: [DMAE–ADAME]
APE: Michael adduct resulting from addition of DMAE on EA: [DMAE+EA]
PTZ: Phenothiazine
4OH-TEMPO: 4-hydroxy-2,2,6,6-tetramethyl piperidinoxyl Example 1 (Comparative)

A glass reactor with mechanical stirrer, heated by an electric flask heater and surmounted by a Vigreux column with condenser, vacuum separator, receiver and trap is charged with 500 g of heavy residue (6) obtained from the outlet of the evaporator (5).
The composition by weight of this residue is as follows:
DMAE: 17.3%—ADAME: 11.9%—APA: 28%—q.s. 100%: heavy fractions+catalyst+inhibitors.
1000 ppm of PTZ and 500 ppm of 4OH-TEMPO are added.

The residue is heated, with stirring and bubbling with nitrogen, for 60 min at 160° C. at an operating pressure from 100 mbar to 30 mbar at the end. The following are recovered:
Distillate: 218 g
Final residue: 262 g
The composition by weight of the distillate is:
DMAE: 48.7%
ADAME: 40.6%
APA: 57%
EA: 1%
Other heavy fractions: q.s. 100%
There is considerable fouling of the reactor and it is impossible to clean. The residue is very viscous when hot and solidifies at room temperature.

Example 2 (According to the Invention)

Example 1 is repeated with addition of 2000 ppm of compound BEYCOSTAT® FB 095, marketed by the company CECA, to the initial charge.
The rest of the treatment is similar to example 1.
There is very little fouling of the reactor, the final residue is viscous but does not solidify at room temperature.

Example 3 (According to the Invention)

A glass reactor with mechanical stirrer, heated by an electric flask heater and surmounted by a Vigreux column with condenser, vacuum separator, receiver and trap is charged with 510 g of heavy residue (6) obtained from the outlet of the evaporator (5).
The composition by weight of this residue is as follows:
DMAE: 2.9%—ADAME: 19.2%—APA: 30.2%—q.s. 100%: heavy fractions+catalyst+inhibitors.
500 ppm of PTZ, 500 ppm of BEYCOSTAT® FB 095 and 1000 ppm of NALCO® EC 3368A marketed by the company NALCO are added.
The residue is heated, with stirring and bubbling with nitrogen, for 65 min at 160-180° C. under an operating pressure of 20 mbar. The following are recovered:
Distillate: 182 g
Final residue: 325 g
The composition by weight of the distillate is:
DMAE: 16.1%
ADAME: 70.2%
APA: 7.5%
APE 3.8%
The composition by weight of the residue is:
DMAE: 11.9%
ADAME: 0.1%
APA: 9.8%
Heavy fractions+catalyst+inhibitors: q.s. 100%
The balances by weight demonstrate the upgrading of ADAME and DMAE recovered during the process according to the invention:
ADAME: for 98 g present in the free state in the residue, 128 g is recovered, a proportion of which is from thermal cracking of APA.
DMAE: for 14.6 g present in the free state in the residue, 68.3 g is recovered, a proportion of which is from thermal cracking of APA.
APA: for 154.2 g present in the residue, only 45.3 g remains after thermal cracking of APA.
The reactor is perfectly clean (no adhering solid) and the final residue is perfectly fluid when hot.
The residue is then cooled to 60° C. and 30% of methanol is added to it.

After this addition, it can be transported by pump without difficulty (viscosity at 60° C.: 50.5 mPa).

Example 4 (According to the Invention)

Example 3 is reproduced using 2000 ppm of NALCO EC3368A. At the end of reaction, the reactor is perfectly clean and the residue remains transportable when hot.

The invention claimed is:
1. A process for recovering noble products comprising dialkylaminoalkyl(meth)acrylate and an amino alcohol, starting from heavy (meth)acrylic fractions generated during the production of (meth)acrylic esters by transesterification, the heavy fractions comprising at least the noble products and Michael adducts resulting from reactions of addition on the (meth)acrylic double bonds, said process comprising the steps of:
  (i) adding at least one antifouling agent and optionally a viscosity-reducing compound to the heavy fractions to form a mixture;
  (ii) submitting the mixture to temperature and distillation conditions sufficient for cracking the Michael adducts into their constituent components without adding acid;
  (iii) recovering the noble products in the form of a stream of distillate, and of a final residue that is sufficiently fluid to be transported by pump,
wherein the antifouling agent is a compound of formula (A):

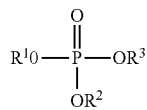

in which:
  $R^1$ represents a $C_3$-$C_{30}$ alkyl radical, an aryl radical or an alkaryl radical, and these radicals can be interrupted or attached to the oxygen of the molecule by a chain —$(OR^4)_o$—, where the $R^4$ each represent independently an ethylene, propylene or butylene chain and o is an integer from 0 to 50;
  $R^2$ represents $R^1$, a hydrogen atom or a counter-ion;
  $R^3$ represents a hydrogen atom or a counter-ion.
2. The process of claim 1, wherein the compounds of formula (A) are selected from those in which $R^1$ and $R^2$ each represent independently the radical

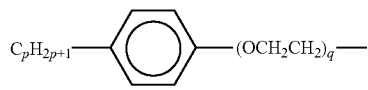

where p is an integer from 4 to 12, and q is an integer from 4 to 50, and $R^3$ represents a hydrogen atom or a counter-ion; and/or
those in which $R^1$ represents the radical

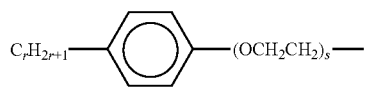

where r is an integer from 4 to 12, and s is an integer from 4 to 50, and $R^2$ and $R^3$ each represent independently a hydrogen atom or a counter-ion.
3. The process of claim 1, wherein the antifouling agent is added in the range from 0.01 to 1 wt % to the heavy fraction to be treated.
4. The process of claim 1, that wherein the conditions of cracking and of distillation comprise a temperature in the range from 100° C. to 250° C.
5. The process of claim 1, wherein viscosity-reducing compound is introduced in an amount sufficient to render final residue from step (ii) pumpable.
6. The process of claim 1, wherein a single compound acting as antifouling agent and viscosity-reducing agent is added in step (i).
7. The process of claim 1, wherein the noble products comprise N,N dimethylaminoethyl acrylate and N,N dimethylaminoethanol.
8. A process for manufacturing a dialkylaminoalkyl(meth) acrylate of formula (I):

$$H_2C=C(R'i)-C(O)-O-A-N(R'_2)(R'_3) \quad (I)$$

in which:
R'i is a hydrogen atom or a methyl radical
A is a linear or branched $C_1$-$C_5$ alkylene radical
$R'_2$ and $R'_3$, which may be identical or different, each represent a $C_1$-$C_4$ alkyl radical, by transesterification reaction between an amino alcohol of formula (II):

$$HO-A-N(R'_2)(R'_3) \quad (II)$$

in which A, $R'_2$ and $R'_3$ are as defined above,
and a light alkyl(meth)acrylate of formula (III):

$$CH_2=C(R'i)-COOR'_4 \quad (III)$$

in which R'i is as defined above and $R'_4$ represents the methyl or ethyl radical;
said process being a transesterification reaction comprising the following steps:
  a) submitting a mixture comprising a compound of formula (III), an amino alcohol of formula (II), a transesterification catalyst, and at least one polymerization inhibitor, to transesterification to form a mixture comprising (meth)acrylic ester (I), the unreacted compounds (II) and (III), the catalyst, the polymerization inhibitor, Michael adducts resulting from reactions of addition on the (meth)acrylic double bonds, and other heavy compounds;
  b) distilling the mixture of products to recover, at the top, an overhead stream comprising a major fraction of the required (meth)acrylic ester (I) and light products, comprising a minor fraction of Michael adducts and heavy products, but free or substantially free from catalyst, and leaving, at the bottom, a heavy fraction comprising the catalyst, the polymerization inhibitor, the Michael adducts and the heavy compounds, with a minor fraction of the required (meth)acrylic ester (I) and amino alcohol and traces of light products;
  c) purifying the overhead stream, giving the purified dialkylaminoalkyl(meth)acrylate (I);
  d) submitting at least a proportion of the heavy fraction to a process for recovery of noble products comprising dialkylaminoalkyl(meth)acrylate and an amino alcohol comprising the steps of: (i) adding at least one antifouling agent and optionally a viscosity-reducing compound; (ii) submitting the mixture to a temperature and distillation conditions sufficient for cracking the Michael adducts into their constituent components without the addition of acid; (iii) recovering the noble products in the form of a stream of distillate, and of a final residue that is sufficiently fluid to be transported by pump;

e) recycling, to the purification step c), at least a proportion of said stream of distillate comprising at least one compound selected from (meth)acrylic ester (I), amino alcohol (II) or alkyl(meth)acrylate (III);

f) disposing the final residue, wherein the antifouling agent is a compound of formula (A):

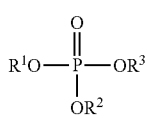

(A)

in which:
- $R^1$ represents a $C_3$-$C_{30}$ alkyl radical, an aryl radical or an alkaryl radical, and these radicals can be interrupted or attached to the oxygen of the molecule by a chain $-(OR^4)_o-$, where the $R^4$ each represent independently an ethylene, propylene or butylene chain and o is an integer from 0 to 50;
- $R^2$ represents $R^1$, a hydrogen atom or a counter-ion;
- $R^3$ represents a hydrogen atom or a counter-ion, added in the range from 0.1 to 1 wt %, to the distillation residue.

9. The process of claim 8, wherein the purification step c) is carried out by two distillation columns in series and wherein at least a proportion of said stream of distillate from step d) is recycled to the top of the first purification column.

10. The process of claim 8 wherein the heavy fraction comprising the catalyst, the polymerization inhibitor, the Michael adducts and the heavy compounds, with a minor fraction of the required (meth)acrylic ester (1) and the amino alcohol and traces of light compounds, is first submitted to purification by passage through a film evaporator prior to step d).

11. The process of claim 8, wherein the conditions of cracking and of distillation comprise a temperature in the range from 100° C. to 250° C.

12. The process of claim 8, wherein the viscosity-reducing compound is introduced in sufficient amount so that the final residue from step (ii) is pumpable.

13. The process of claim 9, wherein the dialkylaminoalkyl (meth)acrylate is N,N-dimethylaminoethyl acrylate.

* * * * *